United States Patent
Ogawa et al.

(10) Patent No.: US 12,136,476 B2
(45) Date of Patent: Nov. 5, 2024

(54) MEDICATION ASSISTANCE INFORMATION PROVIDING DEVICE, METHOD, AND NON-TRANSITORY RECORDING MEDIUM RECORDING PROGRAM

(71) Applicant: OMRON HEALTHCARE Co., Ltd., Kyoto (JP)

(72) Inventors: Hiroshi Ogawa, Kyoto (JP); Asa Hirasawa, Kyoto (JP); Tamio Ueda, Kyoto (JP); Kensuke Ibata, Kyoto (JP); Tomoya Ishida, Kyoto (JP); Hideyuki Kobayashi, Kyoto (JP); Masaki Yamada, Kyoto (JP); Takanobu Yamauchi, Kyoto (JP); Mizuki Furuta, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 356 days.

(21) Appl. No.: 17/448,115

(22) Filed: Sep. 20, 2021

(65) Prior Publication Data
US 2022/0005570 A1    Jan. 6, 2022

Related U.S. Application Data (63) Continuation of application No. PCT/JP2020/008796, filed on Mar. 3, 2020.

(30) Foreign Application Priority Data

Mar. 25, 2019    (JP) .................................. 2019-056546

(51) Int. Cl.
*G16H 20/10*    (2018.01)
*A61B 5/00*    (2006.01)
(Continued)

(52) U.S. Cl.
CPC ........... *G16H 20/10* (2018.01); *A61B 5/4833* (2013.01); *G06Q 30/0206* (2013.01);
(Continued)

(58) Field of Classification Search
CPC ........ G16H 20/10; G16H 10/60; G16H 50/20; G16H 50/70; G16H 70/40; G16H 40/67; A61B 5/4833; G06Q 30/0206
See application file for complete search history.

(56) References Cited

U.S. PATENT DOCUMENTS

| | | | |
|---|---|---|---|
| 6,578,003 B1 * | 6/2003 | Camarda | G16H 20/10 705/2 |
| 2013/0218588 A1 * | 8/2013 | Kehr | G16H 40/63 705/2 |

(Continued)

FOREIGN PATENT DOCUMENTS

| | | |
|---|---|---|
| CN | 105849733 A | 8/2016 |
| JP | 2002-366652 A | 12/2002 |

(Continued)

OTHER PUBLICATIONS

International Search Report for International Application No. PCT/JP2020/008796, dated May 19, 2020.
(Continued)

*Primary Examiner* — Meredith A Long
(74) *Attorney, Agent, or Firm* — Birch, Stewart, Kolasch & Birch, LLP (57) ABSTRACT

The present invention provides prediction information for an effect of taking a medicine on a biometric value. A medication assistance information providing device includes a first acquisition unit configured to acquire prescription information related to a medicine that a user plans to take, a second acquisition unit configured to acquire dosing adherence rate information including a dosing adherence rate
(Continued)

representing a medication achievement of the user with respect to a dosage specified by the prescription information, a third acquisition unit configured to acquire change prediction information for a biometric value of the user relative to the dosing adherence rate on the basis of the prescription information and the dosing adherence rate information, and a first provision unit configured to provide the change prediction information for the biometric value.

13 Claims, 4 Drawing Sheets

(51) Int. Cl.
- *G06Q 30/0201* (2023.01)
- *G16H 10/60* (2018.01)
- *G16H 50/20* (2018.01)
- *G16H 50/70* (2018.01)
- *G16H 70/40* (2018.01)
- *G16H 40/67* (2018.01)

(52) U.S. Cl.
CPC .............. *G16H 10/60* (2018.01); *G16H 50/20* (2018.01); *G16H 50/70* (2018.01); *G16H 70/40* (2018.01); *G16H 40/67* (2018.01)

(56) References Cited

U.S. PATENT DOCUMENTS

| | | | |
|---|---|---|---|
| 2015/0100343 A1* | 4/2015 | Siedlecki | G16H 20/10 705/2 |
| 2016/0132660 A1* | 5/2016 | Barajas | G16H 30/40 705/2 |
| 2016/0203290 A1* | 7/2016 | An | G16H 40/67 705/2 |
| 2017/0004258 A1 | 1/2017 | Wang et al. | |
| 2019/0385723 A1 | 12/2019 | Sato et al. | |

FOREIGN PATENT DOCUMENTS

| | | |
|---|---|---|
| JP | 2015-87956 A | 5/2015 |
| JP | 2017-188075 A | 10/2017 |
| WO | WO 2018/168298 A1 | 9/2018 |
| WO | 2018/235440 A1 | 12/2018 |

OTHER PUBLICATIONS

International Preliminary Report on Patentability mailed Oct. 7, 2021, in PCT/JP2020/008796.

Chinese Office Action and Search Report for Chinese Application No. 202080018905.5, dated Mar. 30, 2024, with an English translation.

* cited by examiner

MEDICATION ASSISTANCE INFORMATION PROVIDING DEVICE, METHOD, AND NON-TRANSITORY RECORDING MEDIUM RECORDING PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2020/008796, filed Mar. 3, 2020, which application claims priority to Japanese Patent Application No. 2019-056546, filed Mar. 25, 2019, which applications are incorporated herein by reference in their entireties.

TECHNICAL FIELD

This invention relates to a medication assistance information providing device, method, and a non-transitory recording medium recording a program.

BACKGROUND ART

Forgetting to take a medicine is a common experience, and apparatuses exist that provide notification to encourage a user to take their medicine. For example, there are apparatuses that use an alarm clock where the apparatus can be set to a time at which medicine is to be taken, and the apparatus lets the user know the timing at which the user should take the medicine.

According to this apparatus, the user for example, can preset the timing at which the medicine should be taken, and when that time is reached, the apparatus can give a notification of an instruction that the medicine should be taken, and the user can take the medicine without forgetting. However, there is a problem in that the user may become accustomed to the notification and let the timing of taking the medicine pass, and eventually a dosing adherence rate decreases and a sustained effect of taking the medicine is reduced.

Thus, as one countermeasure to a user who forgets to take a medicine despite a notification, a medical professional, including a physician, nurse, or the like, could conceivably monitor a dosing status of the user (e.g., a patient). However, because medical personnel are usually responsible for multiple users, realistically, monitoring the dosing status of all users often cannot be accomplished. Also, it is difficult for medical personnel to identify from the user dosing status whether a medicine has been taken according to a predetermined schedule for all users without errors.

Given this, in Patent Document 1, dosing information (dosing content and dosing time) transmitted from a patient terminal stored in a patient medication information storage unit is compared to a medication schedule for each patient stored in the medication information storage unit, which allows an alert determination unit to detect, for example, a patient forgetting to take a medicine, and in a case where forgetting to take the medicine is detected, the server communicates with a physician terminal and provides a notification that the patient is neglecting to take the medicine. The patent document discloses that a physician can sufficiently grasp a patient's dosing status, and therefore the patient can be encouraged to not forget to take a medicine.

CITATION LIST

Patent Literature

Patent Document 1: JP 2002-366652 A

SUMMARY OF INVENTION

Technical Problem

In this manner, with a conventional device (for example, Patent Document 1), medical personnel watch over a patient, detect that a dosing of a medicine has been forgotten, and encourage the user to take the medicine. With this device, if the patient has no intention for taking the medicine, the problem of the dosing adherence rate not increasing is not resolved.

In light of the circumstances described above, one aspect of the present invention is to provide a medication assistance information providing device, method, and program that provide prediction information for an effect of taking a medicine on a biometric value.

Solution to Problem

In order to solve the problem described above, the present disclosure adopts the following configurations.

Namely, a medication assistance information providing device according to a first aspect of the present disclosure includes a first acquisition unit configured to acquire prescription information related to a medicine that a user plans to take, a second acquisition unit configured to acquire dosing adherence rate information including a dosing adherence rate representing a medication achievement of the user with respect to a dosage specified by the prescription information, a third acquisition unit configured to acquire change prediction information for a biometric value of the user relative to the dosing adherence rate on the basis of the prescription information and the dosing adherence rate information, and a first provision unit configured to provide the change prediction information for the biometric value.

In the above configuration, the first acquisition unit acquires the prescription information related to the medicine that the user plans to take. The first acquisition unit acquires the prescription information by, for example, a pharmacist of a pharmacy inputting the prescription information off-line via an input device, or reads a two-dimensional code (for example, a QR code (trade name)) printed on a paper prescription or the like to acquire the prescription information. Note that the prescription information includes a prescription normally recorded on paper describing a medicine prescribed by a physician as well as detailed data related to the medicine, such as, for example, actions and effects, side effects, dosing methods (dosage, time for dosing, and the like), storage methods, lifestyle advisory, standard classification, and approval number.

The second acquisition unit acquires the dosing adherence rate information including the dosing adherence rate, which indicates the medication achievement indicating that the user has taken the medicine (which may also include when the medicine was taken) with respect to the dosage specified by the prescription information. The medication achievement is recording that the user has taken the medicine and may also include a dosing date and time. In addition, by measuring the biometric data of the user, the medication assistance information providing device may also determine whether the user has taken the medicine according to variation in particular biometric data and the determination result may be used as the medication achievement. Biometric data is data related to the living body of the user and is, for example, electrocardiographic data, blood pressure data, heart rate data, or blood glucose level data.

Based on the prescription information and the dosing adherence rate information, the third acquisition unit acquires change prediction information indicating how the biometric value of the user varies relative to the dosing adherence rate. The change prediction information is obtained by a table, which is computed in advance by a server or the like, a program and the like, and is determined on the basis of the prescription information and the dosing adherence rate information, which is the input information. In addition, these tables and/or programs may be stored in the medication assistance information providing device, and the table and/or program may be read from the medication assistance information providing device to acquire the change prediction information.

As described above, according to the medication assistance information providing device according to the first aspect of the present disclosure, the device can present the user with a prediction for a change in efficacy of a medicine relative to the dosing adherence rate, based on the medication achievement of the user taking the prescribed medicine, and therefore the user can know how the user's own biometric value changes depending on the current dosing adherence rate. As a result, when the dosing adherence rate of the user is low, the biometric value indicated by the change prediction information is seen to be deteriorating, providing motivation to increase the dosing adherence rate. On the other hand, when the user has a high dosing adherence rate of approximately 100%, the user sees how the biometric value changes or that the biometric value is in a good state, providing motivation to maintain a high dosing adherence rate. In this way, the medication assistance information providing device according to this aspect is able to increase the user's dosing adherence rate from a low value or to maintain a high value. Thus, according to the medication assistance information providing device, the user continuing to take a medicine can be promoted by providing (presenting, displaying, and/or outputting, for example) a change prediction for the effect or efficacy of the medicine relative to the dosing adherence rate.

Furthermore, the medication assistance information providing device according to the first aspect of the present disclosure may be any device capable of acquiring and providing the change prediction information for the biometric value of the user with the first acquisition unit, the second acquisition unit, and the third acquisition unit, and may be a device that executes these operations as a program, such as a wearable apparatus (for example, a smart phone or a wristwatch-style wearable terminal), an activity meter, or a stationary device (for example, a personal computer). In addition, the medication assistance information providing device may or may not be worn by the user, for example, and it is sufficient that the acquisition units of these devices are capable of acquiring prescription information, user medication achievement, and change prediction information for a biometric value. For example, the user may wear a detection device capable of detecting electrocardiogram, and the medication assistance information providing device may acquire electrocardiographic data (one type of biometric data) from the detection device and execute the program described above.

A medication assistance information providing device according to a second aspect of the present disclosure further includes a generation unit configured to generate, based on the change prediction information for the biometric value, detriment information for the user that is expected when the dosing adherence rate is continued, and a second provision unit configured to provide the detriment information.

In the above configuration, the medication assistance information providing device according to the second aspect generates, based on the change prediction information for the biometric value, the detriment information for the user that is predicted when the current dosing adherence rate is continued, and therefore the user can know content that will pose a future detriment to the user from the current dosing adherence rate. As a result, the user attempts to increase the current dosing adherence rate in order to eliminate the content that will pose a detriment.

In a medication assistance information providing device according to a third aspect of the present disclosure, the generation unit generates, as the detriment information, alarm information representing an advisory or warning to the user.

In the above configuration, the generation unit generates, as the detriment information, the alarm information that represents an advisory or warning to the user, and therefore the user can recognize that the user's biometric value will not improve at the current dosing adherence rate, i.e., with the current medication achievement. In addition, the user receives the advisory or warning from the alarm information, which is an opportunity for the user to reconsider the current medication achievement by viewing, for example, the change prediction information for the biometric value.

In a medication assistance information providing device according to a fourth aspect of the present disclosure, the generation unit generates, as the detriment information, medicine modification prediction information of the prescription information including at least one of an increase in amount of the medicine and a change in type of the medicine.

In the above configuration, the generation unit generates, as the detriment information, the medicine modification prediction information including a prediction that one of an increase in the amount of the medicine and a change in the type of the medicine will occur in the future, and therefore, since the biometric value is not improved with the current medication achievement, the medicine modification prediction information enables the user to view, for example, future prescription information. Because the user can consider detailed prediction information in conjunction with the change prediction information for the biometric value, the medicine modification prediction information provides motivation to increase the current dosing adherence rate for the medicine.

In a medication assistance information providing device according to a fifth aspect of the present disclosure, the generation unit generates, as the detriment information, information predicting an increase in a purchase cost of the medicine.

In the above configuration, the generation unit has a greater likelihood of motivating the user to increase the current dosing adherence rate, since the user, for example, views and considers information that predicts an increase in the purchase cost of the medicine in a case where the current dosing adherence rate is continued.

In a medication assistance information providing device according to a sixth aspect of the present disclosure, the generation unit generates, as the detriment information, information predicting an increase in the probability of occurrence of, or information predicting shortening of the period of time until occurrence of, at least one of severe symptoms and a change in clinical condition.

In the above configuration, with the generation unit, by the user viewing the information that predicts an increase in the probability of occurrence of at least one of severe symptoms and a change in clinical condition, in a case where the current dosing adherence rate is continued, the user can know the likelihood that symptoms may change and become more severe or that a clinical condition may deteriorate if the current dosing adherence rate is not increased. Thus, the detriment information generated by the medication assistance information providing device in this aspect increases the likelihood that the user will be motivated to increase the dosing adherence rate.

In a medication assistance information providing device according to a seventh aspect of the present disclosure, the third acquisition unit acquires the change prediction information from a storage medium storing a predicted characteristic of a change in the biometric value over time for a case where a dosage per medicine is used as a parameter.

In the above configuration, the third acquisition unit acquires the change prediction information from the storage medium that stores a characteristic (for example, a characteristic curve) that predicts a change in the biometric value relative to the passage of time after taking the medicine, with the dosage of each medicine as a parameter. This storage medium is not limited as to which device includes the storage medium, and may be, for example, a storage medium included in a server, a storage device included in the medication assistance information providing device, or the like. Furthermore, the characteristic stored in the storage medium is, for example, respective characteristic for each medicine owned by a pharmaceutical company and predicts a change in a biometric value relative to the passage of time after taking the medicine. Alternatively, even when characteristic data is not the rigorous characteristic data owned by the pharmaceutical company, characteristic data that is useful for increasing the dosing adherence rate of the user is sufficient and may be characteristic data obtained by statistical processing of changes in the dosing adherence rate and the biometric value of other users taking the same medicine. In addition, the characteristic may in some cases be a generic characteristic that is determined for each medicine, and be a characteristic that predicts a change in a biometric value relative to the passage of time after taking the medicine.

A medication assistance information providing device according to an eighth aspect of the present disclosure further includes a correction unit configured to correct the change prediction information on the basis of log data recording a time variation of a biometric value relative to a dosage in the user's past.

In the above configuration, with respect to the change prediction information calculated on the basis of the prescription information and the dosing adherence rate information, the correction unit enables obtaining change prediction information that is more accurate than prior to correction by further correcting the change prediction information on the basis of the log data that records a time variation of the user's biometric value relative to the user's dosage.

Furthermore, even in cases where the same amount of medicine is taken for similar diseases or symptoms, when changes in a biometric value are known to differ due to body build, physical constitution, and other biological factors, the change prediction information can be corrected based on a change in the biometric value and even more accurate change prediction information can be obtained.

The medication assistance information providing device according to yet another aspect is further provided with a display unit configured to display an interface for the user causing to execute inputting the medication achievement.

The above configuration further includes the display unit of the medication assistance information providing device, and the display unit can display an interface for initiating a process for transmitting physician assistance data, and the user can use the interface to input the medication achievement with the medication assistance information providing device. The interface may be anything as long as the user is able to input data for the medication achievement, but is, for example, a button of a graphical user interface (GUI), and the user uses the button of the GUI, for example, to input to the medication assistance information providing device that the user has taken the medicine.

In a medication assistance information providing device according to yet another aspect, the first acquisition unit acquires the prescription information or information for accessing the prescription information as data represented by a two-dimensional code.

In the above configuration, the prescription information is represented by the two-dimensional code and therefore, although the area occupied by text varies when drug information is written with text, the two-dimensional code has substantially the same area for the prescription information for different medicines. The two-dimensional code may encode the text information without modification, may describe a URL to be accessed, or the like. In addition, the two-dimensional code may also be compatible with smart phones and computers in handling data, and recently has been used as a prescription in pharmacies and hospitals. The two-dimensional code can have information in the horizontal and vertical directions (two dimensions), and a greater amount of data can be stored than in a bar code.

In a medication assistance information providing device according to yet another aspect, the device further includes a reception unit configured to receive biometric data including a biometric value by a short-range wireless communication system, and the device receives the biometric data in a case where a transmitting party is authenticated as a preset device.

In the above configuration, the medication assistance information providing device can receive the biometric data by the short-range wireless communication system, and can authenticate that the transmitting party is the preset device and reliably receive the desired biometric data. Note that the short-range wireless communication system is not limited to a particular method and may be any communication method.

In a medication assistance information providing device according to yet another aspect, the two-dimensional code is acquired by an image acquisition unit.

In the above configuration, the two-dimensional code presented by the medication assistance information providing device is acquired by the image acquisition unit, therefore allowing the user to immediately decrypt the two-dimensional code and obtain the prescription information. The image acquisition unit may be connected to the medication assistance information providing device or may be installed in the medication assistance information providing device.

Advantageous Effects of Invention

According to the present invention, in one aspect, a medication assistance information providing device, method, and a non-transitory recording medium recording a program can be provided that provide prediction information for an effect, of taking a medicine, on a biometric value.

DESCRIPTION OF EMBODIMENTS

An embodiment according to an aspect of the present invention (hereinafter, also referred to as "the present embodiment") will be described below with reference to the drawings. Note that, in the following embodiment, parts denoted by the same reference numbers perform the same operations, and a repetitive explanation will be omitted.

Overview

First, with reference to FIG. 1, an overview of a medication assistance information providing device according to the present invention will be described.

Figure 1:
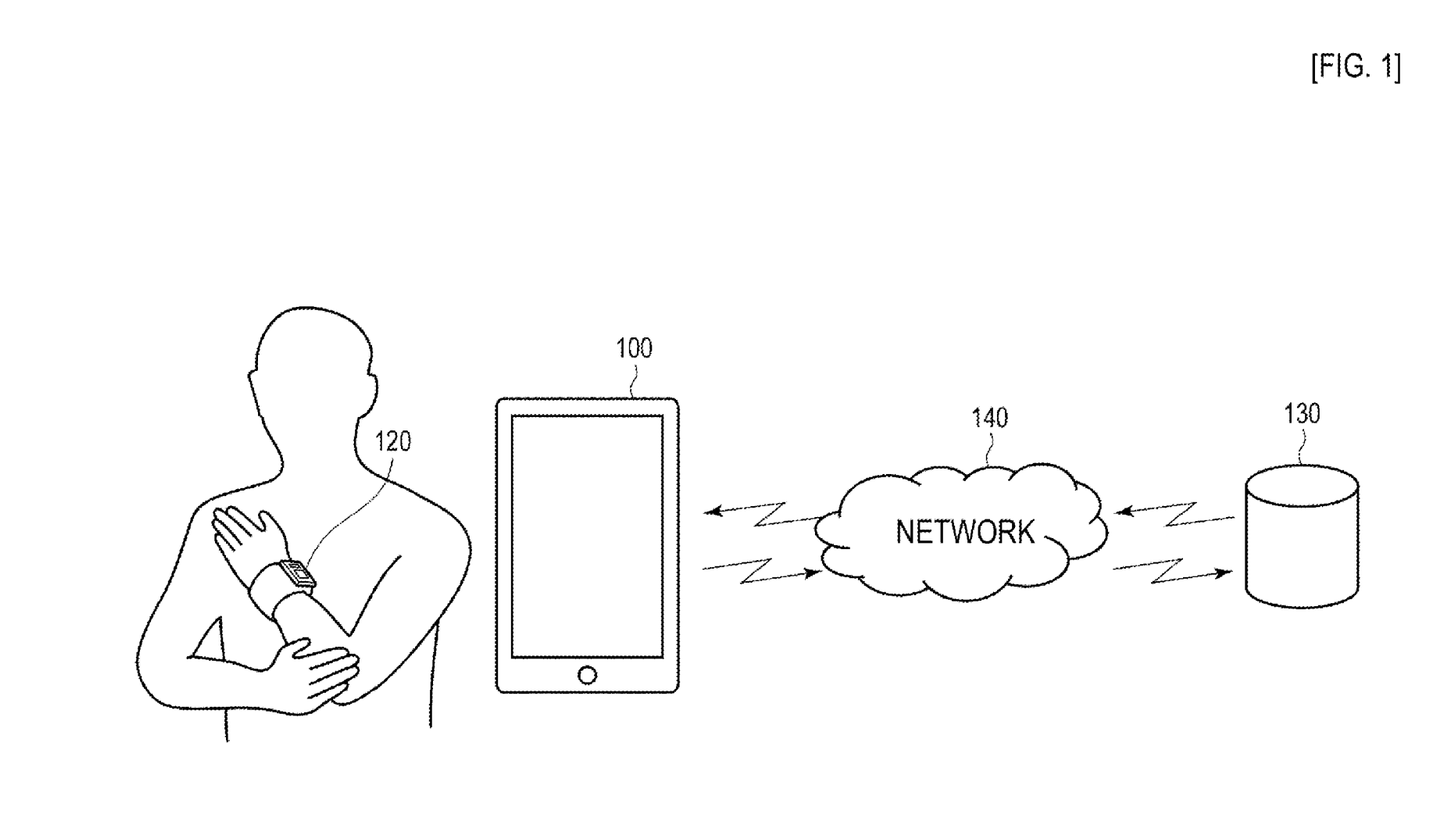
FIG. 1 is a diagram illustrating a schematic of a system according to an embodiment including a medication assistance information providing device, a wristwatch-style wearable terminal, and a server connected via a network.

FIG. 1 schematically illustrates a medication assistance information providing device 100, a wristwatch-style wearable terminal 120, a server 130, and a network 140 according to an exemplary overview. Note that the medication assistance information providing device 100 and the wristwatch-style wearable terminal 120 may have the same function, and that herein, the wristwatch-style wearable terminal 120 can measure biometric data of a user.

The medication assistance information providing device 100 receives a prescription from the user and acquires from the outside server 130, via the network 140, prescription information for a medicine to be taken by the user. The medication assistance information providing device 100 may query a server or the like of a pharmaceutical company for information related to the medicine described in the prescription information, acquire detailed data related to the medicine, and include that data in the prescription information. In addition, the medication assistance information providing device 100 acquires a medication achievement indicating that the user has taken the medicine, associates the medication achievement with the prescription information that has already been acquired, and acquires dosing adherence rate information including a dosing adherence rate for a given medicine. Further, based on the prescription information and the dosing adherence rate information, the medication assistance information providing device 100 acquires change prediction information for a biometric value of the user relative to the dosing adherence rate. The change prediction information indicates a predicted characteristic (for example, expressed by a two-dimensional graph) of a change in a biometric value over time for a case where the dosage per medicine described in the prescription is used as a parameter.

In addition, the medication assistance information providing device 100 acquires biometric value log data that has recorded a time variation of a biometric value relative to a dosage for each medicine in the user's past. The biometric value is, for example, measured by the wristwatch-style wearable terminal 120 and transmitted by short-range wireless communication or the like, and is received by the medication assistance information providing device 100. The medication assistance information providing device 100 may also correct the change prediction information for the user's biometric value based on the acquired biometric value log data.

Moreover, the medication assistance information providing device 100 acquires a current dosing adherence rate for a medicine taken by the user in the (corrected) change prediction information for the user's biometric value and uses the change prediction information at the dosing adherence rate to generate detriment information on a detriment the user may be expected to experience. The medication assistance information providing device 100 then provides the detriment information to the user in a user-customized presentation format (expressed through a display, audio playback, vibration, light, or the like).

Instead of the medication assistance information providing device 100, the wristwatch-style wearable terminal 120 may include a device similar to the medication assistance information providing device 100 and may perform similar operations. In this example, the wristwatch-style wearable terminal 120 is worn by the user to measure a biometric value of the user to generate biometric data, and is set to be capable of transmitting the biometric data to the medication assistance information providing device 100.

The wristwatch-style wearable terminal 120 measures the biometric data of the user by the user wearing (or carrying) the terminal and transmits the biometric data to the medication assistance information providing device 100. The biometric data may be any data related to the living body, such as electrocardiographic data, blood pressure data, and heart rate data. In addition, the desired biometric data of the user is acquired from the wristwatch-style wearable terminal 120. For example, biometric data measured by the external wristwatch-style wearable terminal 120 is obtained via the communication interface 201 at regular intervals. In addition, the biometric data may be continuously measured by constantly connecting with the external wristwatch-style wearable terminal 120 via the communication interface 201 to acquire the biometric data continuously over time. The format of the measurement may be determined depending on the type of biometric data, e.g., the heart rate data is measured continuously over time, and the electrocardiographic data, blood pressure data, and blood glucose level data are measured at regular intervals. In addition, the wristwatch-style wearable terminal 120 acquires the measured data continuously over time or at regular intervals in accordance with the type of data.

For example, in a case where the biometric data is electrocardiographic data, an electric potential difference signal that is indicative of a potential difference between two electrodes and that is output in a time series from a signal processing circuit in the wristwatch-style wearable terminal 120 is acquired as the electrocardiographic data. In this example, the electrocardiographic data is a waveform signal that represents electrical activity of the heart. When the biometric data is blood pressure data, blood pressure data (time series data including systolic blood pressure (SBP) and diastolic blood pressure (DBP)) measured by the wristwatch-style wearable terminal 120 is acquired.

The server 130 connects to and exchanges data with the medication assistance information providing device 100 via the network 140. The server 130 is, for example, a server in a hospital, and generates and stores prescription information.

Note that in a case where the medication assistance information providing device 100 can independently detect the biometric data detected by the wristwatch-style wearable terminal 120, the biometric data detected by the medication assistance information providing device 100 may be used. In such a case, the medication assistance information providing device 100 includes a device portion that calculates the biometric data of the wristwatch-style wearable terminal 120.

As described above, according to the medication assistance information providing device of the present embodiment, the dosing adherence rate is calculated from the performance of the user taking a prescribed medicine and the change prediction information for the biometric value that indicates the efficacy of the medicine relative to the dosing adherence rate is acquired. Then, the sort of change in the biometric value that may occur in the future in a case where the user continues with the current dosing adherence rate can be applied to the change prediction information and provided to the user. Thus, since prediction information for a future change in the biometric value can be known in advance for a case where the user continues with the current dosing adherence rate, when the dosing adherence rate is low, the user's intention is more likely to change to attempt to increase the dosing adherence rate and the information provides motivation to maintain the dosing adherence rate when the dosing adherence rate is already high.

As a result, according to the present medication assistance information providing device, the likelihood of raising the dosing adherence rate of the user is expected to increase, and missed doses are expected to decrease due to the user's awareness improving. According to the present medication assistance information providing device, rather than an external device or medical personnel forcibly compelling the user to take medicine, the dosing adherence rate improves due to changes in the user's own intention, and therefore confidence in the user's health care increases and the likelihood of a permanent improvement in dosing adherence rate rather than a temporary improvement increases.

Configuration Example

Hardware Configuration
Medication Assistance Information Providing Device

Next, an example of a hardware configuration of the medication assistance information providing device 100 (or the wristwatch-style wearable terminal 120) according to the present embodiment will be described using FIG. 2.

Figure 2:
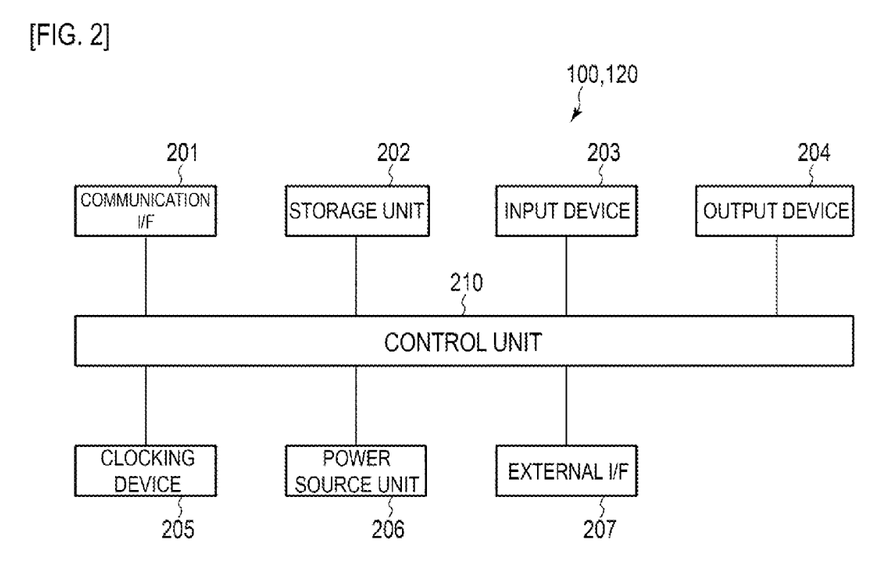
FIG. 2 is a diagram schematically illustrating an example of a hardware configuration of the medication assistance information providing device according to the embodiment.

As illustrated in FIG. 2, the medication assistance information providing device 100 (or the wristwatch-style wearable terminal 120) according to the present embodiment includes a computer in which the communication interface 201, a storage unit 202, an input device 203, an output device 204, a clocking device 205, a power source unit 206, an external interface 207 are electrically connected to a control unit 210. The medication assistance information providing device 100 according to the present embodiment is equivalent to the "medication assistance information providing device" of the present invention. Note that, in FIG. 2, the communication interface and the external interface are described as "communication I/F" and "external I/F", respectively.

The communication interface 201 is an interface for wired or wireless communication via a network, such as a short-range wireless communication (e.g., Bluetooth (trade name)) module, a wired local area network (LAN) module, or a wireless LAN module. The communication interface 201 is an interface for connecting the medication assistance information providing device 100 to an external device (e.g., a computer or a communication apparatus on a network; in the example of FIG. 1, a wristwatch-style wearable terminal 120 and a server 130). The communication interface 201 is controlled by the control unit 210, and is for receiving and acquiring, from the server 130 via the network 140 for example, the change prediction information for the biometric value relative to the dosing adherence rate. In addition, the communication interface 201 is for acquiring, with the wristwatch-style wearable terminal 120 measuring the user's biometric value, the biometric data including the measured user's biometric value from the wristwatch-style wearable terminal 120. The medication assistance information providing device 100 also uses the communication interface 201 when simply viewing incentive data and/or physician assistance data without downloading the data. Further, the medication assistance information providing device 100 may also transmit the prescription information and/or medication data indicating the medication achievement of the user to the server 130 via the network 140, compute the dosing adherence rate on the server 130, and calculate the change prediction information for the user's biometric value on the basis of the prescription information and the dosing adherence rate information, and the medication assistance information providing device 100 may acquire the change prediction information.

The communication via the network may be wireless or wired. Note that the network may be an internetwork including the Internet, another type of network such as an intra-hospital LAN, or may be one-to-one communication using a Universal Serial Bus (USB) cable or the like. The communication interface 201 may include a micro USB connector.

The storage unit 202 is a medium that accumulates information about a recorded program and the like by electrical, magnetic, optical, mechanical, or chemical action such that the information about the program and the like can be read by a computer, another device, a machine, and the like. The storage unit 202 may be, for example, an auxiliary storage device such as a hard disk drive or a solid state drive. The storage unit 202 stores information acquired by the communication interface 201, the input device 203, and the like. This information includes, for example, prescription information of the medicine, the medication achievement data of the user, and the change prediction information for the biometric value relative to the dosing adherence rate.

In addition, the storage unit 202 stores an execution program executed by the control unit 210, the program being used to acquire the prescription information related to the medicine, dosage information for the user, the dosing adherence rate information for the user, the change prediction information for the user's biometric value, and the predicted characteristic (data indicative of the predicted characteristic) of the change in the biometric value over time for a case where the dosage for each medicine is used as a parameter.

Furthermore, biometric data including a time history of the biometric values acquired by the wristwatch-style wearable terminal 120 or the like may have all of the biometric data for a predetermined period of time stored in the storage unit 202.

The input device 203 is a device such as, for example, a touch panel, a physical button, a mouse, or a keyboard, which receives input. The output device 204 is a device that performs output, and outputs information with a display, audio, print medium, light, or the like and is a display, a speaker, or a printer, for example. The touch panel is capable of inputting information by touching a display panel with a finger, a pen, or the like and also displays buttons to be touched and other information, and the touch panel therefore corresponds to both the input device 203 and the output device 204.

The clocking device 205 is a device that measures time, and can measure date and time. For example, the clocking device 205 may be a clock including a calendar, and passes current date and time information to the control unit 210.

The power source unit 206 may be any power source capable of supplying power, for example, an AC power source that can be acquired from a rechargeable secondary battery or an ordinary outlet. The power source unit 206 supplies power to each element installed in a body of the medication assistance information providing device 100. The power source unit 206 supplies power to the communication interface 201, the storage unit 202, the input device 203, the output device 204, the clocking device 205, the external interface 207, and the control unit 210, for example.

The external interface 207 intervenes between an exterior and the body of the medication assistance information providing device 100, which is a USB port, for example, and is an interface for connecting to an external device (e.g., a memory, a communication apparatus, a biometric data measurement device, or a server). The external interface 207 is an interface for connecting to an external device, such as a server, an electrocardiograph, a blood pressure monitor, a pedometer, an activity meter, and/or an acceleration sensor, for example.

The control unit 210 includes a central processing unit (CPU), a random-access memory (RAM), a read-only memory (ROM), and the like, and controls each component in accordance with information processing. The storage unit 202 stores the execution program that is for acquiring the prescription information related to the medicine, the dosage information for the user, the dosing adherence rate information for the user, the change prediction information for the user's biometric value, and the predicted characteristic (data indicative of the predicted characteristic) of the change in the biometric value over time for a case where the dosage for each medicine is used as a parameter, and the control unit 210 invokes the execution program from the storage unit 202 and executes the process. Details of the control unit 210 will be described with reference to FIG. 3.

Software Configuration

Medication Assistance Information Providing Device 100

Figure 3:
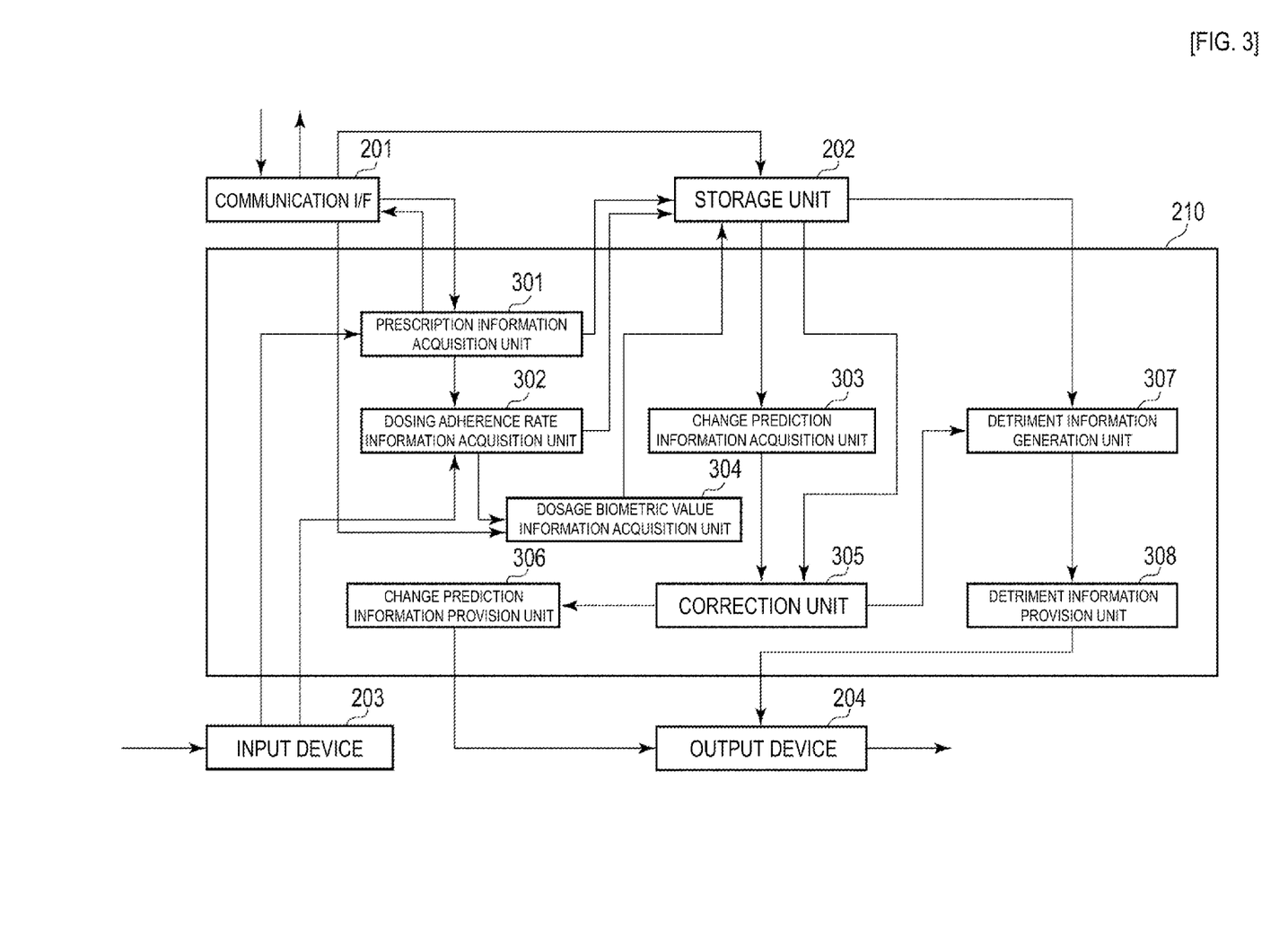
FIG. 3 is a diagram illustrating an example of a portion of a software configuration of the medication assistance information providing device according to the embodiment.

Next, an example of a software configuration of the medication assistance information providing device 100 according to the present embodiment will be described using FIG. 3. FIG. 3 illustrates a software configuration for executing the program executed by the control unit 210 of the medication assistance information providing device 100, the program being used to acquire the prescription information related to the medicine, the dosage information for the user, the dosing adherence rate information for the user, the change prediction information for the user's biometric value, and a predicted characteristic (data indicative of the predicted characteristic) of the change in the biometric value over time for a case where the dosage for each medicine is used as a parameter.

When executing a necessary program, the control unit 210 of the medication assistance information providing device 100 deploys into RAM the execution program that is stored in the storage unit 202 and that acquires the prescription information related to the medicine, the dosage information for the user, the dosing adherence rate information for the user, the change prediction information for the user's biometric value, and the predicted characteristic (data indicative of the predicted characteristic) of the change in the biometric value over time for a case where the dosage for each medicine is used as a parameter. Then, the control unit 210 uses the CPU to interpret and execute the execution program deployed in the RAM and controls each component. In this way, as illustrated in FIG. 3, the medication assistance information providing device 100 according to the present embodiment includes a prescription information acquisition unit 301, a dosing adherence rate information acquisition unit 302, a change prediction information acquisition unit 303, a dosage biometric value information acquisition unit 304, a correction unit 305, a change prediction information provision unit 306, a detriment information generation unit 307, and a detriment information provision unit 308.

The prescription information acquisition unit 301 acquires the prescription information of the medicine taken by the user from the outside server 130 via the communication interface 201. The server 130 is, for example, a server in a hospital, and generates and stores prescription information. In addition, the prescription information acquisition unit 301 may acquire the prescription information via the input device 203. The user may input a prescription received from a hospital via the input device 203 while off-line, or may use an input device 203 that is an image acquisition device to acquire a two-dimensional code printed on the prescription, and decode the code to acquire the prescription information. Furthermore, data regarding the medicine may also be acquired from a hospital server or the like via the communication interface 201 and may be acquired as the prescription information.

In addition, the prescription information acquisition unit 301 may query a server or the like of a pharmaceutical company via the communication interface 201 for information related to the medicine described in the prescription information, acquire detailed data related to the medicine, and include this data in the prescription information. The detailed data related to the medicine may be any information related to the medicine, but includes, for example. The prescription information acquired by the prescription information acquisition unit 301 is stored in the storage unit 202.

The dosing adherence rate information acquisition unit 302 acquires via the input device 203 the medication achievement indicating that the user has taken the medicine, associates the medication achievement with the prescription information acquired by the prescription information acquisition unit 301, and acquires the dosing adherence rate information including the dosing adherence rate for a given medicine. The medication achievement is data that is input and recorded through the input device 203 by the user indicating that the user has taken a given medicine. The dosing adherence rate information acquisition unit 302 can acquire from the prescription information the usage and dosage of the medicine to be taken by the user, and therefore can calculate the dosing adherence rate indicating the medication achievement for a specified dosage using the history of taking the medicine from the input device 203. The dosing adherence rate information acquisition unit 302 stores the acquired dosing adherence rate information in the storage unit 202.

The dosing adherence rate information acquired by the dosing adherence rate information acquisition unit 302 is stored in the storage unit 202 in association with the prescription information acquired by the prescription information acquisition unit 301. In addition, the storage unit 202 stores the change prediction information for the user's biometric value relative to the dosing adherence rate on the basis of the prescription information and the dosing adherence rate information. The prescription information acquisition unit 301 accesses the server 130 of the pharmaceutical company, hospital, or the like, through the communication interface 201, provides the prescription information, acquires the change prediction information for the biometric value relative to the dosing adherence rate for the medicine described in the prescription, and stores the change prediction information in the storage unit 202. The server 130 stores the predicted characteristic of the change in the biometric value over time for a case where the dosage for each medicine is used as a parameter, and is updated each time data related to the medicine is updated. Additionally, the information about the medicine described in the prescription and the dosing adherence rate information may be provided to the server 130 and, on the server 130, only the change prediction information for the biometric value relative to a particular dosing adherence rate may be acquired from among the change prediction information, without storing the change prediction information for each medicine in the storage unit 202.

The change prediction information acquisition unit 303 acquires, from the storage unit 202, the change prediction information for the user's biometric value relative to the dosing adherence rate based on the prescription information acquired by the prescription information acquisition unit 301 and the dosing adherence rate information acquired by the dosing adherence rate information acquisition unit 302.

The dosage biometric value information acquisition unit 304 acquires biometric value log data that has recorded a time variation of the biometric value relative to the dosage for each medicine in the user's past, and sequentially stores the acquired biometric value log data in the storage unit 202. The dosage biometric value information acquisition unit 304 acquires biometric data from the biometric data measurement device, such as the wristwatch-style wearable terminal 120, via the communication interface 201, acquires dosing information of the medicine taken by the user from the dosing adherence rate information acquisition unit 302, and acquires biometric value log data from these information.

The correction unit 305 corrects the change prediction information acquired by the change prediction information acquisition unit 303 on the basis of the biometric value log data acquired by the dosage biometric value information acquisition unit 304 and stored in the storage unit 202. Biometric value log data is more user-customized data since the data is created based on actual user dosing information. As a result, the correction unit 305 makes a correction based on the biometric value for the actual taking of the medicine by the user, and therefore data that is closer to the user's genuine change prediction information can be obtained.

The change prediction information provision unit 306 provides the change prediction information corrected by the correction unit 305 to the user via the output device 204. The change prediction information provision unit 306 may provide the change prediction information to the user in any form, for example, taking dosing adherence rate as a parameter and generating a graph with time as the horizontal axis and the biometric value of the user to be improved by the medicine as the vertical axis, and generating data for the change prediction information that uses a data format that can be displayed on the output device 204. The graph predicts a numerical value that tracks with a biometric value at any given dosing adherence rate. In addition, the change prediction information provision unit 306 may generate the data format of the change prediction information such that the information may be printed by a printer, the output device 204 may be used as a printer, and the output device 204 may output the information using a paper medium or the like. As an example of other formats, the change prediction information provision unit 306 may employ audio, for example, and provide the change prediction information to the user by reproducing the change prediction information with audio.

The detriment information generation unit 307 acquires the current dosing adherence rate for a medicine taken by the user, which is stored in the storage unit 202, in the change prediction information corrected by the correction unit 305, and uses the change prediction information at the dosing adherence rate to generate the detriment information the user may be expected to experience. The detriment information may be any information assumed to be detrimental to the user, and may be, for example, alarm information representing an advisory or warning to the user, medicine modification prediction information for the prescription information, cost increase prediction information that predicts an increase in the purchase cost of a medicine to be taken, and deterioration prediction information that predicts an increase in the probability of occurrence of, and/or predicts shortening of the period of time until occurrence of, severe symptoms and/or changes in clinical condition. The detriment information generation unit 307 passes this generated detriment information to the detriment information provision unit 308.

The detriment information provision unit 308 provides the detriment information generated by the detriment information generation unit 307 to the user via the output device 204. The detriment information provision unit 308 may provide the detriment information to the user in any form, for example, generating data for the detriment information that uses a data format that can be displayed on the output device 204. In a case where the detriment information is the alarm information, the detriment information provision unit 308 generates audio information and outputs the generated audio information to the output device 204. The alarm information may emit light instead of audio, or both audio and light, in which case the detriment information provision unit 308 generates data for outputting audio and/or light. In a case where the detriment information is the medicine modification prediction information, the detriment information provision unit 308 determines a modification to the dosage or type of the medicine that is to be modified based on the current dosing adherence rate, and generates data for displaying this information about the modified medicine or for reproducing the information via audio. The information about the medicine that can be modified is, for example, the prescription information, and the detriment information provision unit 308 generates data for the prescription information to be displayed or reproduced via audio.

In a case where the detriment information is the cost increase prediction information, the detriment information provision unit 308 generates data for displaying a diagram of time graphed versus an increase amount in purchase cost between a medicine currently being taken and a medicine that is highly likely to be taken in the future, or data for presenting the user via audio with an amount by which the purchase cost increases over time. Also, In a case where the detriment information is the deterioration prediction information, the detriment information provision unit 308 generates data for displaying a graph that forecasts how the symptoms of the user may deteriorate in stages with the current dosing adherence rate and illustrates the symptoms in stages relative to time or illustrates the probability of severe symptoms and/or changes in clinical condition occurring relative to time, or generates audio data for expressing the data with audio. Further, if the detriment information is the deterioration prediction information, the detriment information provision unit 308 generates data for displaying the prediction that the time until severe symptoms and/or occurrence of changes in clinical condition is shortening, in a graph relative to time, which illustrates the period with the highest probability from the present until severe symptoms and/or changes in clinical condition are expected to occur, or generates audio data indicating this period over time.

These graphs predict how the detriment information changes with time at a current dosing adherence rate. In addition, the change prediction information provision unit 306 may generate a data format of the detriment information such that the information can be printed by a printer, which is a form of the output device 204, and the output device 204 may output the information using a paper medium or the like.

Other

Operations of the medication assistance information providing device 100 will be described in detail in an operation example described below. Note that in the present embodiment, the control unit 210 of the medication assistance information providing device 100 may be achieved by a general-purpose CPU. Nevertheless, all or a portion of the above operations (or functions) may also be achieved by one or a plurality of dedicated processors. Further, structures in the medication assistance information providing device 100 may be omitted, substituted, and added as appropriate in accordance with the embodiment.

Operation Example Overall

Next, an overview of operations of the medication assistance information providing device 100 will be described using FIG. 4.

Figure 4:
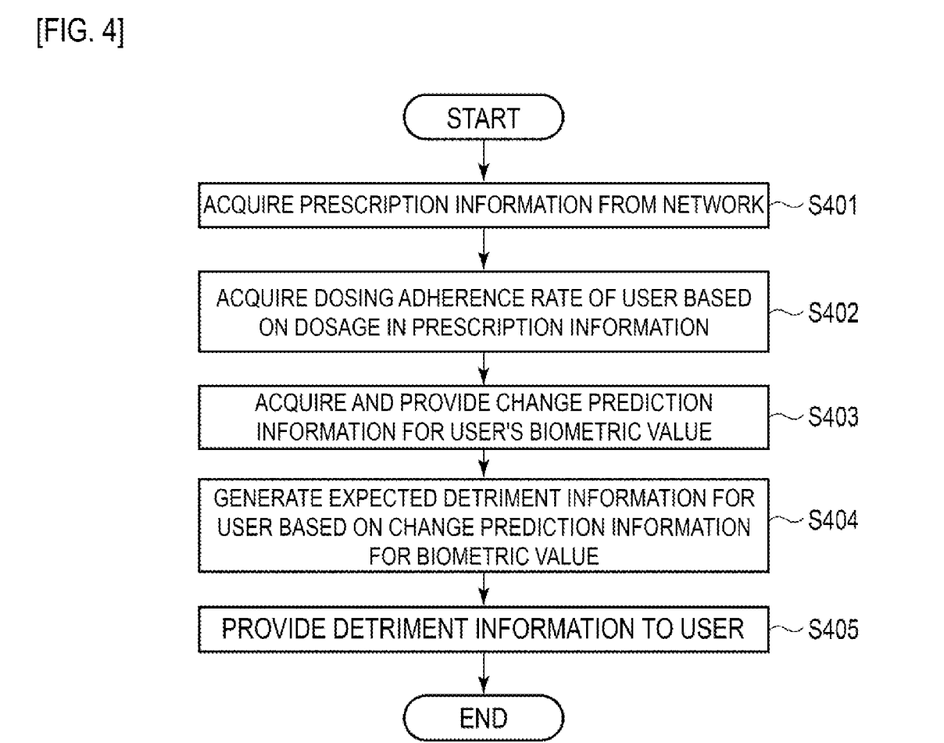
FIG. 4 is a flowchart schematically illustrating an example of a processing procedure related to the medication assistance information providing device according to the embodiment.

FIG. 4 is a flowchart illustrating an example of a processing procedure of the medication assistance information providing device 100. Note that the processing procedure described below is merely an example, and each process may be changed to the extent possible. Further, in the processing procedure described below, steps can be omitted, substituted, and added in accordance with the embodiment as appropriate.

Activation

First, the user activates the medication assistance information providing device 100 via the input device 203, which additionally receives input such as settings. The control unit 210 of the medication assistance information providing device 100 advances the process according to the following processing procedure.
Step S401

In step S401, the control unit 210 operates as the prescription information acquisition unit 301 and acquires the prescription information from a server or the like of an outside pharmaceutical company, via the communication interface 201. The prescription information acquisition unit 301 acquires a prescription describing the name, usage, and the like of the medicine to be taken by the user, which was input with the input device 203, and acquires prescription information including information about the medicine described in the prescription from a server or the like according to the name of the medicine written in the prescription.
Step S402

In step S402, the control unit 210 operates as the dosing adherence rate information acquisition unit 302, acquires via the input device 203 the medication achievement indicating that the user has taken the medicine, associates the medication achievement with the prescription information acquired by the prescription information acquisition unit 301, and acquires the dosing adherence rate information including the dosing adherence rate for a given medicine.
Step S403

In step S403, the control unit 210 operates as the change prediction information acquisition unit 303 and the change prediction information provision unit 306 and acquires the change prediction information for the user's biometric value on the basis of the prescription information and the dosing adherence rate information stored in the storage unit 202, and the change prediction information provision unit 306 provides the change prediction information to the user with the output device 204.

Note that the correction unit 305 may also acquire the change prediction information from the change prediction information acquisition unit 303 and pass to the change prediction information provision unit 306 the corrected change prediction information in which the change prediction information has been corrected on the basis of the user's biometric value log data, and the change prediction information provision unit 306 may provide the corrected change prediction information via the output device 204.
Step S404

In step S404, the control unit 210 operates as the detriment information generation unit 307, acquires the current dosing adherence rate of the medicine being taken by the user that is stored in the storage unit 202, and uses the change prediction information at the dosing adherence rate to generate detriment information the user may be expected to experience.
Step S405

In step S405, the control unit 210 operates as the detriment information provision unit 308 and, via the output device 204, provides the user with the detriment information generated by the detriment information generation unit 307. The detriment information provision unit 308 may also provide the detriment information to the user in any form.

Note that the correction unit 305 may also acquire the change prediction information from the change prediction information acquisition unit 303 and pass to the detriment information generation unit 307 the change prediction information in which the change prediction information has been corrected on the basis of the user's biometric value log data, and the detriment information provision unit 308 may provide the detriment information to the user via the output device 204.

Actions and Effects

As described above, in the medication assistance information providing device 100 according to the present embodiment, in step S401 the prescription information acquisition unit 301 can receive a prescription from the user or the like, and acquire the prescription information including detailed information for the medicine from the server 130 of a pharmaceutical company and the like, via the communication interface 201. Further, in step S402, the dosing adherence rate information acquisition unit 302 can acquire the dosing adherence rate information, and in step S403 can acquire and provide to the user the change prediction information for the user's biometric value on the basis of the dosing adherence rate information and the prescription information. By knowing the change prediction information, the user can predict how much the biometric value may deteriorate when the dosing adherence rate is low, which provides strong motivation to increase the dosing adherence rate. On the other hand, in a case where the dosing adherence rate is high and the biometric value is predicted to improve, motivation can be provided for the user to be satisfied with the present intake and to maintain the dosing adherence rate.

In addition, in step S404, the change prediction information for the biometric value is expected to deteriorate and detriment information on the type of detriment is acquired, and the user can learn about the detriment information in step S405. Thus, since the user can know in advance what sort of detriment may occur when the user continues with the current dosing adherence rate, the dosing adherence rate is more likely to increase.

Modified Examples

While embodiments of the present invention have been described in detail above, the foregoing description is merely illustrative of the present invention in all respects. Of course, various modifications and variations can be made without departing from the scope of the present invention. For example, the following changes are possible. Further, specific configurations according to the embodiment may be adopted as appropriate in the implementation of the invention. Note that, in the following, the same reference numerals are used for components that are the same as those of the above-described embodiment, and descriptions thereof are omitted as appropriate. The following modified examples can be combined as appropriate.

<1>

A sensor detecting the biometric data of the user is installed in the wristwatch-style wearable terminal 120, for example, but the medication assistance information providing device 100 may be provided with these devices, and the dosage biometric value information acquisition unit 304 may acquire biometric data from these devices.

For example, the biometric data may be electrocardiographic data or blood pressure data. Electrocardiographic data is data indicating electrical excitation of the heart and a time change over which the excitation subsides, and electric potential changes due to variable electric fields generated on a body surface by electrical excitation of the heart. Blood pressure data is time series data that include systolic blood pressure (SBP) and diastolic blood pressure (DBP).

When the biometric data is step-count data, the sum of the number of steps is calculated every hour for the number of steps taken by the user in that period of time. In the case of step-count data, the measurement time is also referenced. In a case where there are almost no steps (for example, the sum of the number of steps per hour is continuously equal to or less than a threshold value for a predetermined number of cycles) despite being in daytime, the dosing adherence rate information acquisition unit 302 determines that the number of steps indicates anomaly.

<2>

The data may be transmitted based on a user instruction, e.g., an interface is displayed on the input device 203, and when the user, for example, touches the display, the prescription information acquisition unit 301 sets up the transmission and the prescription is transmitted to the server 130 via the communication interface 201, and the prescription information is received from the server 130 via the communication interface 201.

The dosage biometric value information acquisition unit 304 sets the user's biometric data to be received by the short-range wireless communication system, authenticates that a transmitting party is the wristwatch-style wearable terminal 120, and thus receives the biometric data, making it possible to reliably receive the desired biometric data of the user. This short-range wireless communication system is not limited to a particular method, and may be any desired communication method, including, for example, Bluetooth (trade name) or near field communication (NFC).

<3>

The dosage biometric value information acquisition unit 304 may be configured to authenticate between wristwatch-style wearable terminals 120 that transmit biometric data to the medication assistance information providing device 100 via the communication interface 201, and in a case where a wristwatch-style wearable terminal 120 is authenticated as being the wristwatch-style wearable terminal 120 from which the medication assistance information providing device 100 is to acquire biometric data, the dosage biometric value information acquisition unit 304 may be configured to enable the medication assistance information providing device 100 to receive the biometric data from the wristwatch-style wearable terminal 120.

<4>

The device of the present invention may also be realized by a computer and a program, and the program may be recorded in a recording medium (or storage medium), or provided through a network.

Further, the above-described devices and the device portions thereof can each be implemented by either a hardware configuration or a combined configuration of a hardware resource and software. As the software of the combined configuration, a program is used which is installed from a network or a computer-readable recording medium (or storage medium) into a computer ahead of time, and is executed by a processor of the computer, thereby allowing the computer to achieve the operations (or functions) of the respective devices.

<5>

Note that this invention is not limited to the embodiments described above, and can be embodied by modifying the components in an implementation stage without departing from the gist thereof. Additionally, various inventions can be formed by appropriately combining a plurality of components disclosed in the embodiments described above. For example, some components may be omitted from all the components described in the embodiments. Further, the components of the different embodiments may be combined appropriately.

<6>

Further, "and/or" means any one or more items of the items connected and listed by the "and/or" statement. As a specific example, "x and/or y" means any element of the set of three elements {(x), (y), (x, y)}. As another specific example, "x, y, and/or z" means any element of the set of seven elements {(x), (y), (z), (x, y), (x, z), (y, z), (x, y, z)}.

Supplementary Note 1

A medication assistance information providing device including a first acquisition unit (301) configured to acquire prescription information related to a medicine that a user plans to take, a second acquisition unit (302) configured to acquire dosing adherence rate information including a dosing adherence rate representing a medication achievement of the user with respect to a dosage specified by the prescription information, a third acquisition unit (303, 305) configured to acquire change prediction information for a biometric value of the user relative to the dosing adherence rate on the basis of the prescription information and the dosing adherence rate information; and a first provision unit (306) configured to provide the change prediction information for the biometric value.

REFERENCE SIGNS LIST

100 Medication assistance information providing device
120 Wristwatch-style wearable terminal
130 Server
140 Network
201 Communication interface
202 Storage unit
203 Input device
204 Output device
205 Clocking device
206 Power source unit
207 External interface
210 Control unit
301 Prescription information acquisition unit
302 Dosing adherence rate information acquisition unit
303 Change prediction information acquisition unit
304 Dosage biometric value information acquisition unit
305 Correction unit
306 Change prediction information provision unit
307 Detriment information generation unit
308 Detriment information provision unit

The invention claimed is:

1. A medication assistance information providing system comprising:
    a wearable terminal configured to measure a biometric value of a user wearing the wearable terminal; and
    one or more processors configured to:
        acquire prescription information related to a medicine that a user plans to take;
        acquire dosing adherence rate information including a dosing adherence rate representing a medication achievement of the user with respect to a dosage specified by the prescription information;
        acquire change prediction information for the biometric value of the user relative to the dosing adherence rate on the basis of the prescription information and the dosing adherence rate information; and
        provide the change prediction information for the biometric value.

2. The medication assistance information providing system according to claim 1, wherein the one or more processors are further configured to:
    generate, based on the change prediction information for the biometric value, detriment information for the user that is expected when the dosing adherence rate is continued, and provide the detriment information.

3. The medication assistance information providing system according to claim 2, wherein the one or more processors are further configured to generate, as the detriment information, alarm information representing an advisory or warning to the user.

4. The medication assistance information providing system according to claim 2, wherein the one or more processors are further configured to generate, as the detriment information, medicine modification prediction information of the prescription information including at least one of an increase in amount of the medicine and a change in type of the medicine.

5. The medication assistance information providing system according to claim 2, wherein the one or more processors are further configured to generate, as the detriment information, information predicting an increase in a purchase cost of the medicine.

6. The medication assistance information providing system according to claim 2, wherein the one or more processors are further configured to generate, as the detriment information, information predicting an increase in the probability of occurrence of, or information predicting shortening of the period of time until occurrence of, at least one of severe symptoms and a change in clinical condition.

7. The medication assistance information providing system according to claim 1, wherein the one or more processors are further configured to acquire the change prediction information from a storage medium storing a predicted characteristic of a change in the biometric value over time for a case where a dosage per medicine is used as a parameter.

8. The medication assistance information providing system according to claim 1, wherein one or more processors are further configured to correct the change prediction information on the basis of log data recording a time variation of a biometric value relative to a dosage in the user's past.

9. The medication assistance information providing system according to claim 1,
    wherein the biometric value of the user is received from the wearable terminal that measures the biometric value, and
    wherein one or more processors are further configured to correct the change prediction information for the user's biometric value received from the wearable terminal on the basis of log data recording a time variation of a biometric value relative to a dosage in the user's past.

10. The medication assistance information providing system according to claim 9,
    wherein the biometric value measured by the wearable terminal is received by the one or more processors of the medication assistance information providing system continuously over time or at regular time intervals, and
    wherein the biometric value is one of a heart rate data, an electrocardiogramata, a blood pressure data, and a blood glucose level data.

11. The medication assistance information providing system according to claim 9, wherein the one or more processors are further configured to:
    generate, based on the change prediction information for the biometric value, detriment information for the user that is expected when the dosing adherence rate is continued, and
    provide the detriment information in a user-customized presentation format to the user through at least one of a display, audio playback, vibration, and light.

12. A non-transitory recording medium recording a program for causing a computer to execute functions of the one or more processors in the medication assistance information providing system according to claim 1.

13. A medication assistance information providing method comprising:
- measuring a biometric value of a user via a wearable terminal;
- acquiring, via one or more processors of a medication assistance information providing device, prescription information related to a medicine that a user plans to take;
- acquiring, via the one or more processors, dosing adherence rate information including a dosing adherence rate representing a medication achievement of the user with respect to a dosage specified by the prescription information;
- acquiring, via the one or more processors, change prediction information for a the biometric value of the user relative to the dosing adherence rate on the basis of the prescription information and the dosing adherence rate information; and
- providing, via the one or more processors, the change prediction information for the biometric value.

* * * * *